United States Patent [19]

Kenneth

[11] Patent Number: 4,845,987

[45] Date of Patent: Jul. 11, 1989

[54] CERVICAL MUSCLE EXERCISING AND TESTING APPARATUS

[75] Inventor: F. Scott Kenneth, New Port Richey, Fla.

[73] Assignee: Wanamax Ventures, Inc., Tampa, Fla.

[21] Appl. No.: 231,780

[22] Filed: Aug. 12, 1988

[51] Int. Cl.$^4$ .............................................. A61B 5/22
[52] U.S. Cl. ............................... 73/379; 272/DIG. 5; 128/774
[58] Field of Search .......................... 128/774; 73/379; 272/DIG. 5, 94, 134

[56] References Cited

U.S. PATENT DOCUMENTS

| | | |
|---|---|---|
| 3,752,144 | 8/1973 | Weigle .................................. 73/379 |
| 4,161,946 | 7/1979 | Zuesse . |
| 4,337,780 | 7/1982 | Metrick . |
| 4,702,108 | 10/1987 | Amundsen et al. . |
| 4,732,038 | 3/1988 | DelGiorno et al. . |
| 4,732,381 | 3/1988 | Skowronski . |

Primary Examiner—Donald O. Woodiel
Assistant Examiner—Hollis T. Chen
Attorney, Agent, or Firm—Hoffmann & Baron

[57] ABSTRACT

An apparatus and method are provided for exercising and/or testing the cervical muscles and nerves. The apparatus includes a seat, a shoulder stabilizing assembly, and an assembly for positioning a pressure transducer in proximity to the patient's head. The positioning assembly includes a ring which supports the transducer. The ring is pivotable about a pair of different axes to allow all cervical muscle groups to be tested. The transducer is movable radially within the ring and can be locked in position adjacent the head of the patient. The stabilizing assembly includes restraining members which are either rigid in construction, or in the form of belts, or a combination of belts and rigid parts. An exercise or testing program may be conducted by restraining the patient's shoulders while he applies pressure to the transducer with his head. In this manner, muscles outside the cervical groups will not be recruited during the exercise program or test.

27 Claims, 7 Drawing Sheets

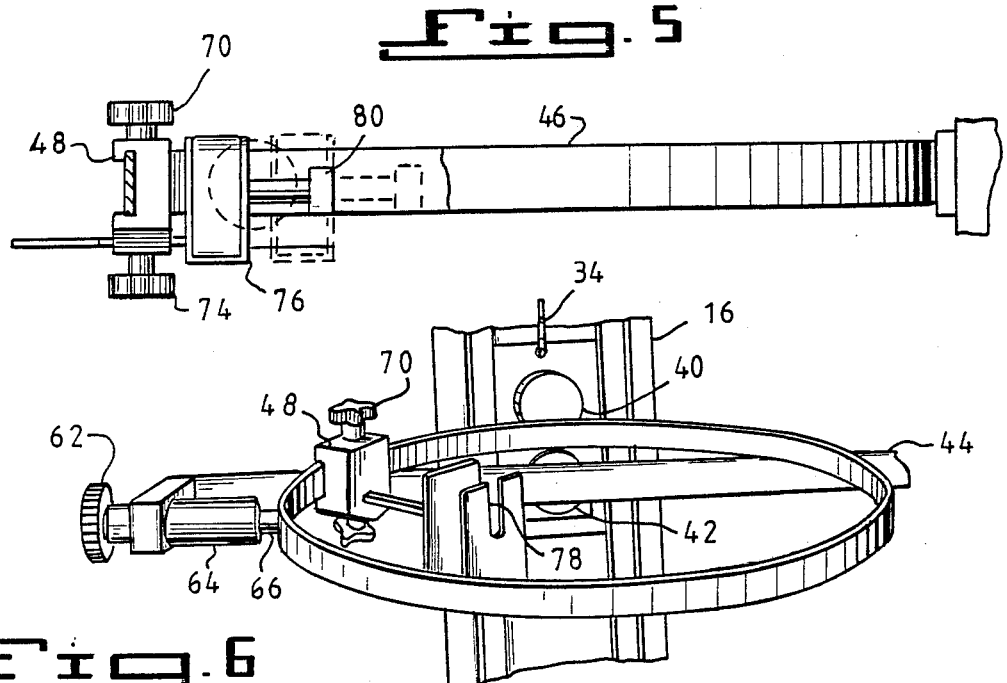
Fig. 5
Fig. 6
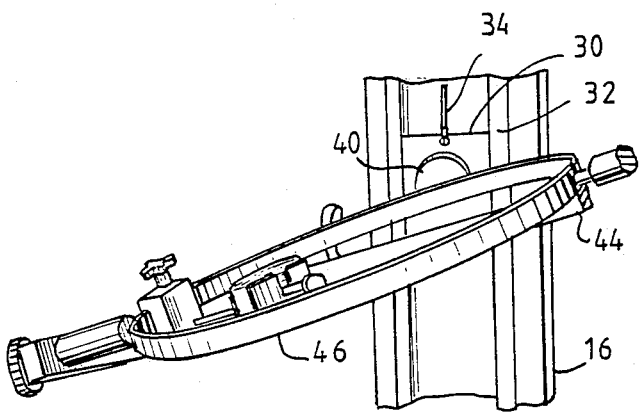
Fig. 7
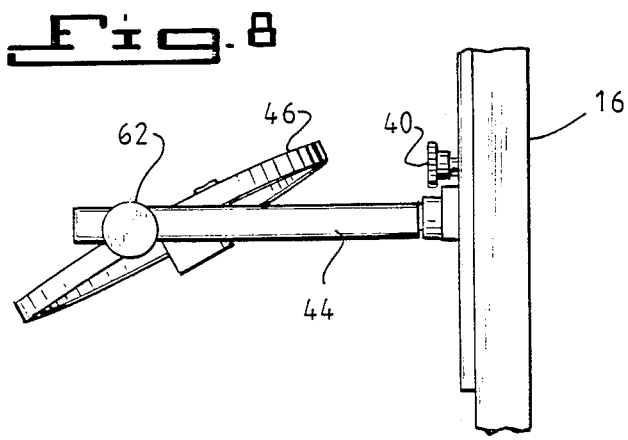
Fig. 8

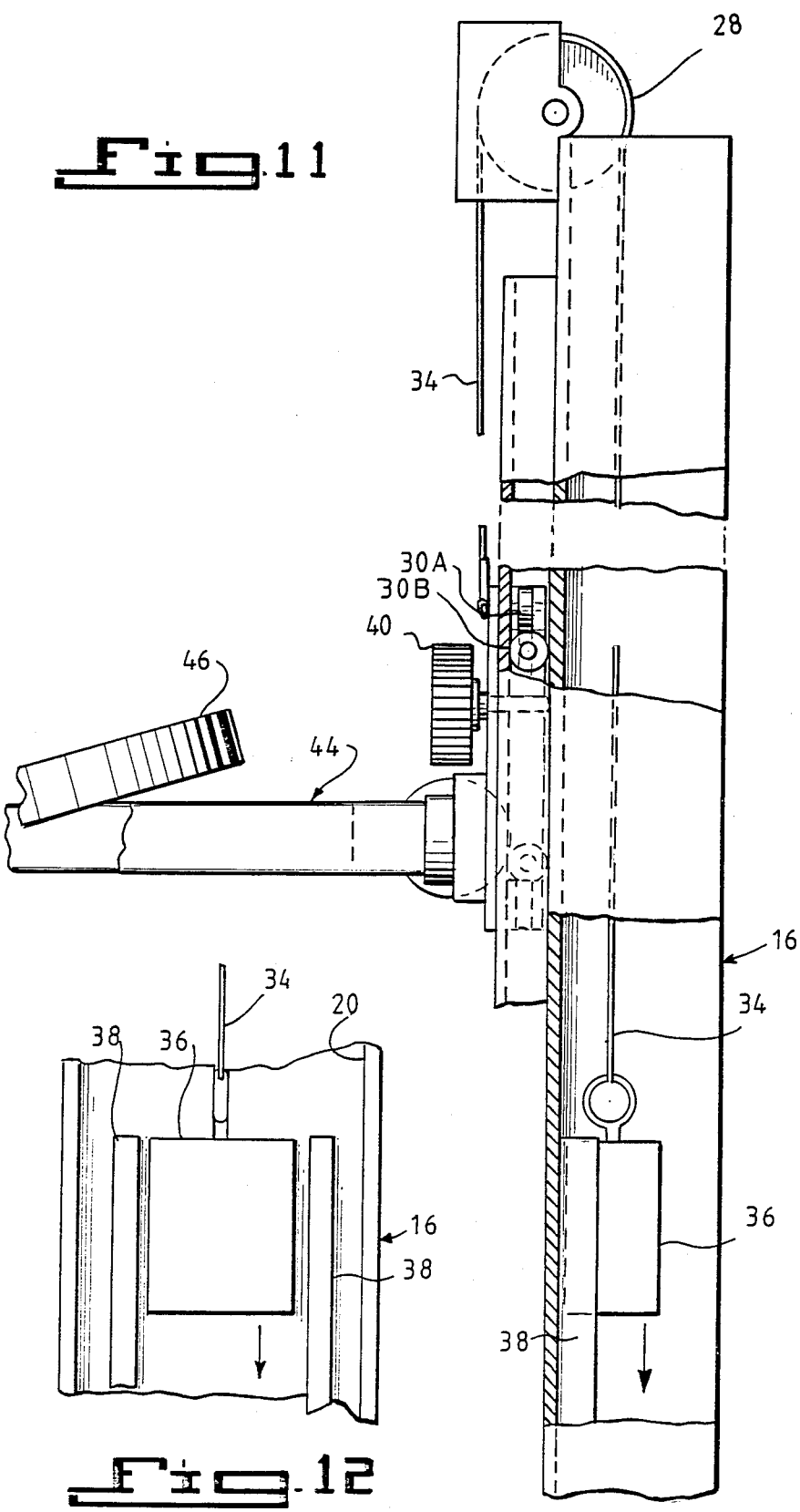

CERVICAL MUSCLE EXERCISING AND TESTING APPARATUS

BACKGROUND OF THE INVENTION

The invention relates to an apparatus and method for exercising or testing the muscles and nerves within the cervical area of the body.

Muscle exercising and testing apparatus have been designed for testing various muscles and muscle groups. They enable a physician or physical therapist to determine which, if any, muscle or nerve groups are not functioning correctly, and provide quantitative indications of whether a patient is responding to therapy. Such apparatus may also be used in conjunction with an exercise program to allow an athlete to determine his progress in increasing the strength of specific muscle groups.

Regardless of the part of the body which is tested, it has long been recognized that the tested muscle or muscle group should be isolated to the greatest possible degree. In other words, the parts of the body not being tested should be maintained in a stable position so that they do not influence the test results.

U.S. Pat. Nos. 4,702,108, 4,732,038 and 4,732,381 disclose equipment for testing and/or exercising various muscle groups. The first-mentioned patent concerns a chair apparatus including stabilization means for immobilizing various parts of the body including the pelvis, thorax, thighs, and legs. Transducers are mounted to six different track systems and adjustably positioned with respect thereto to allow the selected muscle groups to be tested. A transducer mounted to an anterior track is provided for measuring neck flexion while a second transducer mounted to a posterior track measures neck extension.

U.S. Pat. No. 4,732,038 discloses a muscle testing method wherein a sensing means in the form of a pressure pad is supported by a rigid support plate. A selected muscle or muscle group is flexed to apply force against the sensing means. The sternocleidomastoid muscles, which are used for either rotating the head or bending the head forward, are tested by locating the pressure pad to one side of the subject's head with the support plate at a 25°–30° angle with the vertical to test rotation. The pressure pad faces the subject when testing the ability of this muscle to pivot the head forward.

U.S. Pat. No. 4,732,381 is directed to an exercise machine for exercising the lower back muscles. The machine includes a curved chest pad and a scapula pad. The user exerts a rotational force against these pads while in the seated position.

Isometric therapy has been gaining increasing acceptance among physical therapists. Such therapy involves measuring the peak strength or force capable of being exerted by a muscle or muscle group, and then exerting a force for selected periods of time which is less than the measured peak force. It is accordingly necessary to provide an apparatus capable of providing a quantitative indication of the force being exerted by a muscle both during the testing and exercising procedures.

One area of the body which is often subject to injury, strain or other problems is the neck. Muscles associated with neck movement include the sternocleidomastoid, splenius capitis, levator scapulae, and trapezius. Acting individually, the sternocleidomastoid muscles rotate the head. They are also capable of raising the head against a resistive force, such as when one raises his head from a prone position. The splenius capitis muscles are used to pull the head back when acting in unison. Used individually, the head may be rotated or inclined.

Apparatus for testing various neck muscles have included a pressure transducer mounted to an arm. A person applies force to the transducer by pressing the head against the transducer. The force is measured and displayed to the person or therapist. Conventional testing equipment has not, however, provided adequate isolation of the neck muscles being tested. Other muscles are too easily recruited, thereby causing inaccurate results.

The positioning of the pressure transducer with respect to the head is also important. In order to accurately determine whether progress is being made during physical therapy, the transducer should be in the same locations each time a person is tested. Conventional cervical muscle exercise and testing equipment have not included transducer positioning means which allow the user to precisely position the transducer each time the equipment is used.

SUMMARY OF THE INVENTION

It is an object of the invention to provide an apparatus which can be used for isometric therapy of the cervical muscles and which also can be employed as a reliable testing device.

It is another object of the invention to provide an apparatus which will satisfactorily stabilize a person's body to allow the cervical muscles to be isolated for exercising and testing.

In accordance with these and other objects of the invention, an apparatus is provided which includes a support, a positioning ring mounted to the support, and a transducer mounting assembly slidably mounted to the positioning ring. Means are preferably provided for pivoting the ring with respect to the support. Further means are provided for adjusting the height of the support and for pivoting the support about a selected axis.

An assembly for stabilizing a person's body, thereby allowing the cervical muscles to be properly exercised and/or tested is also provided. The stabilizing assembly includes a seat, means for stabilizing the upper chest, waist and pelvic areas, and means for stabilizing the shoulder areas. A transducer mounting assembly is supported above the seat and may be moved adjacent to the head of a person in the seated position.

A method for exercising the cervical muscles may be practiced using the apparatus described above. The subject's body is stabilized such that the neck muscles may be exercised with virtually no chance of recruitment of other muscle groups. The person applies force against a pressure transducer with his head for selected periods of time. While applying such force, a visual and/or audial indication of the magnitude thereof is provided by the apparatus. This insures that the proper force is applied during the exercise period.

A similar method may be employed for testing individual cervical muscles or muscle groups. Once the cervical muscles are effectively isolated through the stabilization of the appropriate parts of the body, they may be tested by having the subject apply maximum pressure against a pressure transducer with his head. The transducer is moved to a number of preselected locations to allow testing of specific muscle groups.

BRIEF DESCRIPTION OF THE DRAWINGS

FIG. 5 is a side elevation view of a transducer supporting apparatus;

FIG. 6 is a top perspective view thereof;

FIG. 7 is a top perspective view thereof showing said transducer supporting apparatus in an inclined position;

FIG. 8 is a side elevation view thereof;

FIG. 11 is a side elevation view of the top portion of the apparatus;

FIG. 12 is a rear elevation view of a portion thereof;

DETAILED DESCRIPTION OF THE INVENTION

Figure 1:
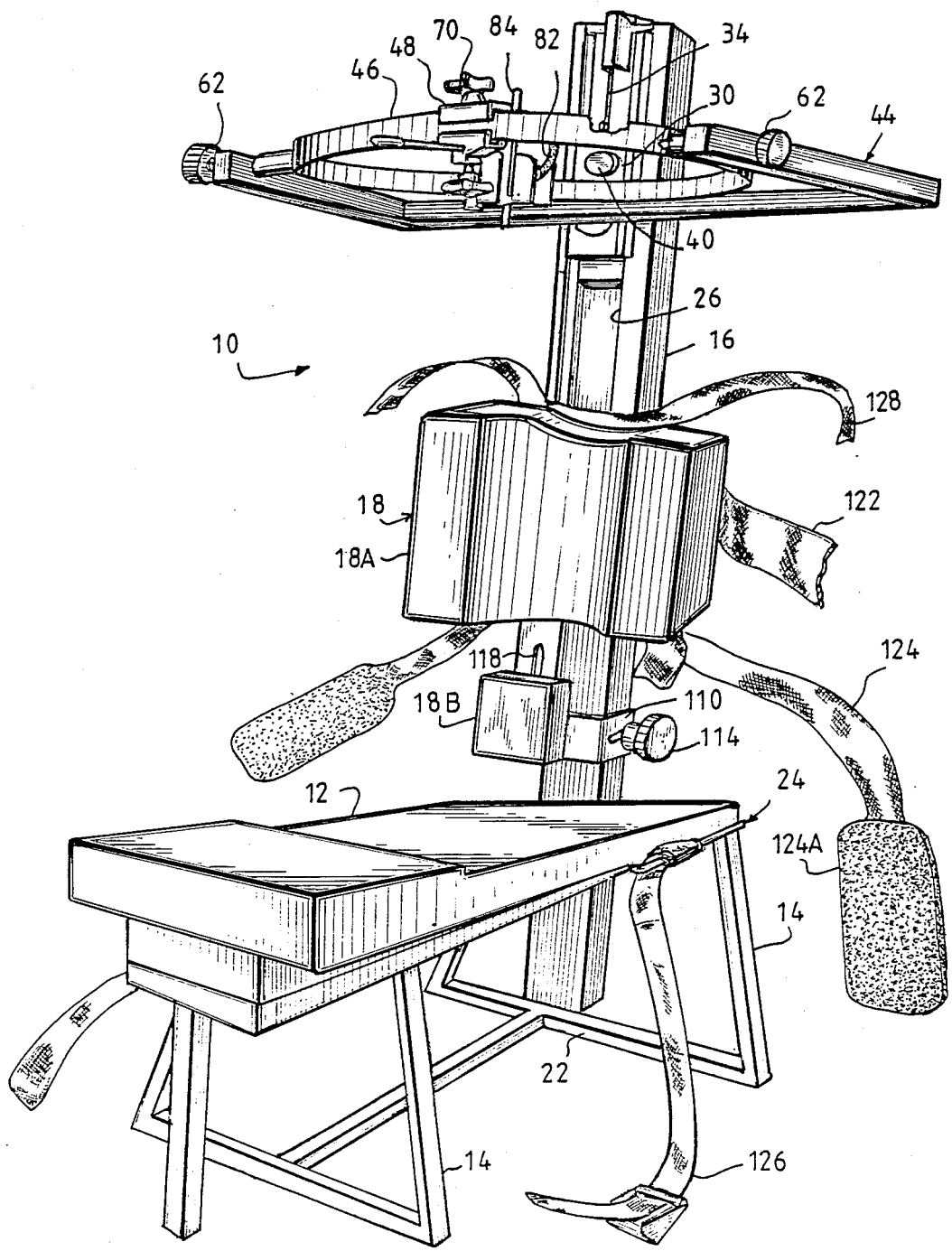
FIG. 1 is a perspective view of cervical muscle exercising and testing apparatus in accordance with the invention.
Figure 2:
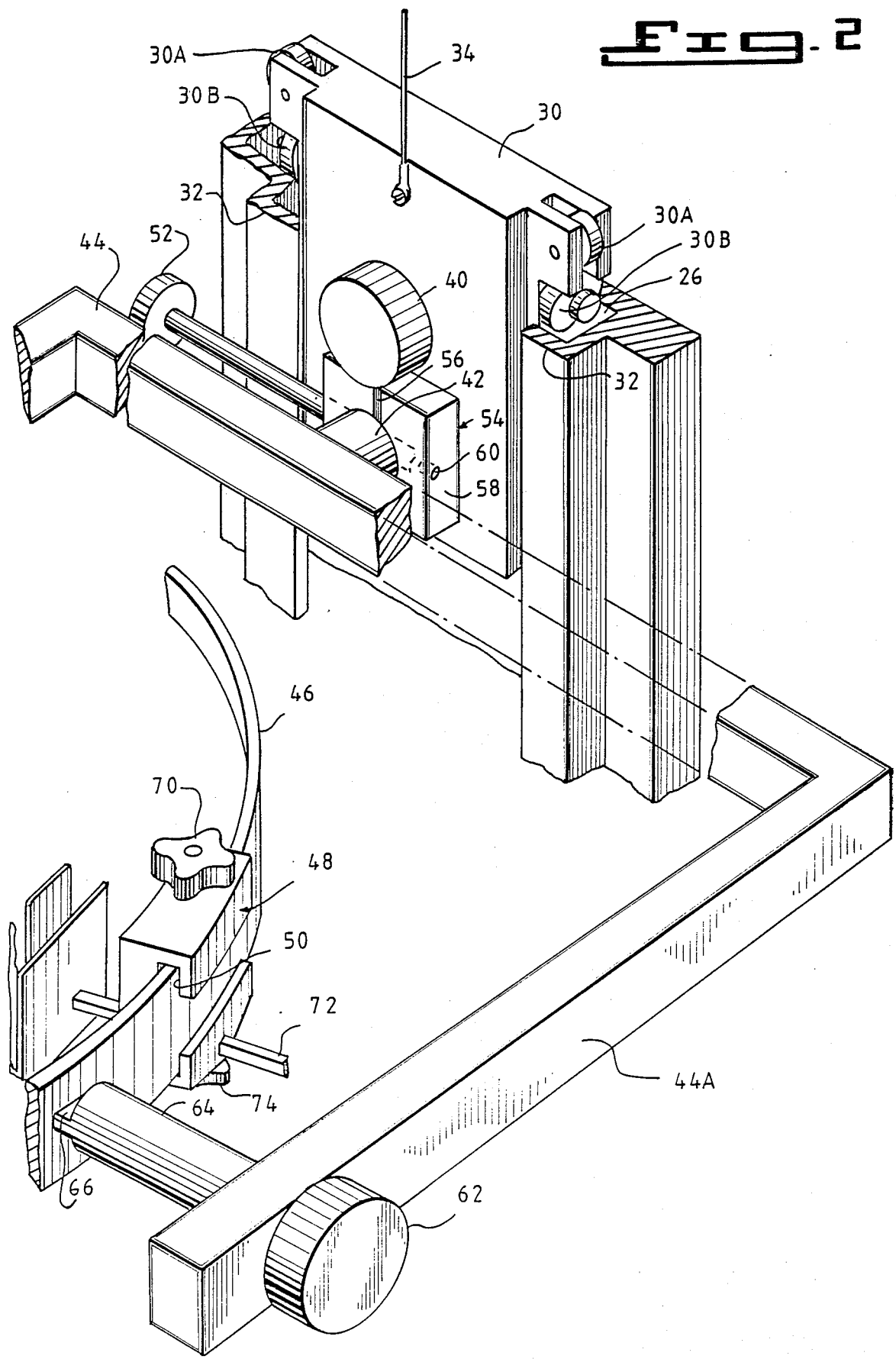
FIG. 2 is an enlarged, top perspective view of a first transducer supporting assembly mounted to the apparatus.

A cervical muscle exercising and testing apparatus 10 is provided which is capable of isolating the neck muscles from the other muscles of the body, thereby allowing such muscles to be exercised using a preselected force or analyzed. The isolation of the neck muscles and the ability to position a pressure transducer with precision insures that any test results will be both accurate and reproducable.

In accordance with a first embodiment of the invention, the apparatus 10 includes a seat 12 supported by a plurality of legs 14, a column 16, and a seat back 18 supported by the column. The seat back includes an upper thoracic support 18A having a center depression formed therein and a lumbar support 18B. The column is made from aluminum or another relatively light weight material having the requisite strength. It has a generally U-shaped cross section which defines a rear channel 20 as shown in FIG. 12. The column is bolted to a cross piece 22 connecting the two rear legs 14 and to the rear of the seat frame 24. A column height of about six feet provides adequate space for the assemblies which are mounted thereto. The width of the column may be about six inches while the depth is about four inches.

A vertically oriented track 26 is mounted to the front face of the column while a pulley 28 (shown in FIG. 11) is mounted near the top thereof. A block assembly 30 is slidably mounted to the track, each side of the block including two pairs of bearings 30A, 30B which abut the opposing surfaces defined by a pair of C-shaped track members 32. A cable 34 is trained about the pulley 28 and is connected at one end to the block assembly 30 and at its opposite end to a counterweight 36 positioned within the rear channel 20. A pair of retaining rods 38 secured to the rear surface of the column 16 prevent excessive lateral displacement of the counterweight. The vertical position of the block assembly 30 is maintained by a tightening knob 40 mounted thereto. The tightening knob includes a pin extending therefrom which bears against the front surface of the column.

A substantially cylindrical pivot member 42 is rotatably mounted within the block assembly 30 and projects a short distance beyond the front surface thereof. The closed end of a generally U-shaped support 44 is secured to the pivot member at the midpoint thereof. The support 44 is accordingly pivotable about the axis of rotation of the pivot member. A transducer positioning ring 46 is pivotably mounted to the opposing arms of the support. The ring is pivotable about an axis running substantially perpendicular to the axis about which the support is pivotable.

The support is made from rectangular aluminum tubing. The ring 46 is substantially rectangular in cross section and supports a transducer positioning member 48. One end of the positioning member 48 defines a substantially T-shaped slot 50 within which the ring 46 is positioned. One or more bearings 48A are mounted to the positioning member to facilitate sliding it about the ring. The weight of the block assembly 30 and the components mounted thereto is substantially the same or slightly less than that of the counterweight 36. The support 44 accordingly must be pushed to lower it with respect to the column 16.

A second tightening knob assembly 52 extends laterally from a rectangular plastic housing 54 extending from the block assembly 30 and is used for locking the pivot member 42 in a desired angular position. The pivot member is supported by the plastic housing 54 which includes a split upper end portion, the split 56 extending between the upper surface of the housing 54 and the top of the cylindrical pivot member 42. A plate 58 is secured to the lateral side of the plastic housing 54 opposite to that from which the second knob assembly extends. The plate 58 includes an opening 60 for receiving one end of a threaded shaft which extends from the knob assembly and through the split upper end portion of the plastic housing. As the knob is turned in one direction, the split 56 narrows and the housing 54 extends pressure on the pivot member 42. The pivot member may accordingly be locked in a selected position ranging between plus and minus thirty degrees from horizontal.

The angular orientation of the transducer positioning ring 46 is set by turning one of a pair of tightening knobs 62 extending laterally from each side of the support 44. Each knob is secured to a cylindrical member 64 which is, in turn, secured to the ring 46 by a flat projection 66 extending therefrom. The flat projection 66 extends within the C-shaped slot 50 of the transducer positioning member 48 when this member is in alignment with the projection 66. The structure for mounting the ring 46 to the support 44 accordingly does not interfere with the process of sliding the transducer positioning member between any two points on the ring. Additional transducer positioning members may be mounted to the ring if desired.

To lock the ring in a desired angular position with respect to the support 44, one or both knobs 62 are turned in appropriate directions to cause them to be drawn towards the respective cylindrical members 64. The frictional forces generated by these members with respect to the two opposing arms 44A of the support prevents the ring 46 from moving with respect thereto. The knobs 62 are loosened by turning them in the opposite directions, thereby causing the knob screws (not shown) within the cylindrical members to be with-drawn. A washer may be provided between each knob 62 and the adjacent support arm 44A to promote frictional contact therebetween. Means (not shown) may be provided for locking the ring in positions coplanar with the support or at thirty degree angles with respect thereto. Such means may include a spring-loaded locking pin which would snap into one of three openings corresponding to the three usual exercise or test positions of the ring.

The transducer positioning member 48 is provided with a tightening knob 70 extending from its upper surface. This knob includes a screw (not shown) extending therefrom which bears against the ring 46 to secure the member 48 in a fixed position thereon. The knob may be turned to withdraw the screw a sufficient distance to allow the user to slide the member 48 to a desired position on the ring. The ring is preferably provided with indicia to designate the correct locations for performing specific muscular exercises or tests. They also allow tests to be accurately reproduced.

A plunger 72 extends from the transducer positioning member 48 towards the center of the ring 46. The user may slide the plunger in either direction along its longitudinal axis. A tightening knob 74 is provided for locking the plunger in a desired axial position.

Figure 3:
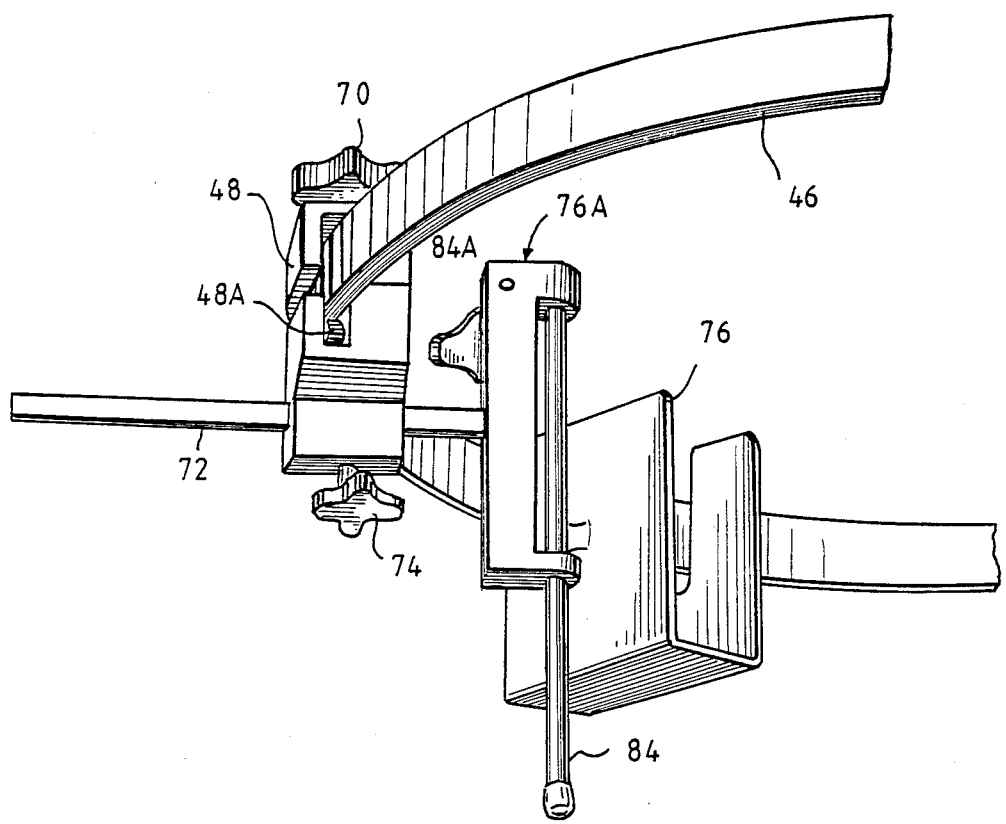
FIG. 3 is a bottom, perspective view of a second transducer supporting assembly which may be mounted to the apparatus.

A mounting bracket 76 (or bracket supporting member 76A as shown in FIGS. 1 and 3) is secured to the end of the plunger. The mounting bracket includes a substantially U-shaped housing, the inner housing wall including a slot 78 therein. A conventional pressure transducer 80 (as shown in FIG. 5) is mounted to the bracket 76. A helical wire 82 extends between the transducer 80 and the appropriate analytical and/or recording equipment (not shown) for providing a digital readout and/or printed results. A digital readout is preferable during isometric therapy to insure the patient is applying the proper force against the bearing surface of the transducer at all times. Alternatively, the mounting bracket may be secured to a rod 84 extending perpendicular to the plane defined by the ring 46. The rod is movable along its longitudinal axis with respect to this plane and also pivotable about this axis. A tightening knob 84A is provided for tightening or loosening the engagement of the rod with respect to the supporting member 76A. The upper portion of the supporting member may include a split portion (not shown) similar to that in block 54.

A stabilizing assembly is provided to insure that muscles other than the cervical muscles are not recruited when the apparatus is in use. In accordance with a preferred embodiment of the invention, a plurality of belts are provided for stabilizing the shoulders, upper chest, waist and pelvis of the patient. Three substantially horizontally extending belts 122, 124 and 126 extend about the upper chest, waist and pelvis of a person, respectively. A fourth pair of belts 128 extend about the shoulders and the seat back. Stability is checked by having the subject move his head and neck to various positions to determine whether other muscles are recruited. If so, the assembly is readjusted to correct the problem. Hook and loop type fastening members 124A may be employed for securing each belt portion about a person.

Figure 13:
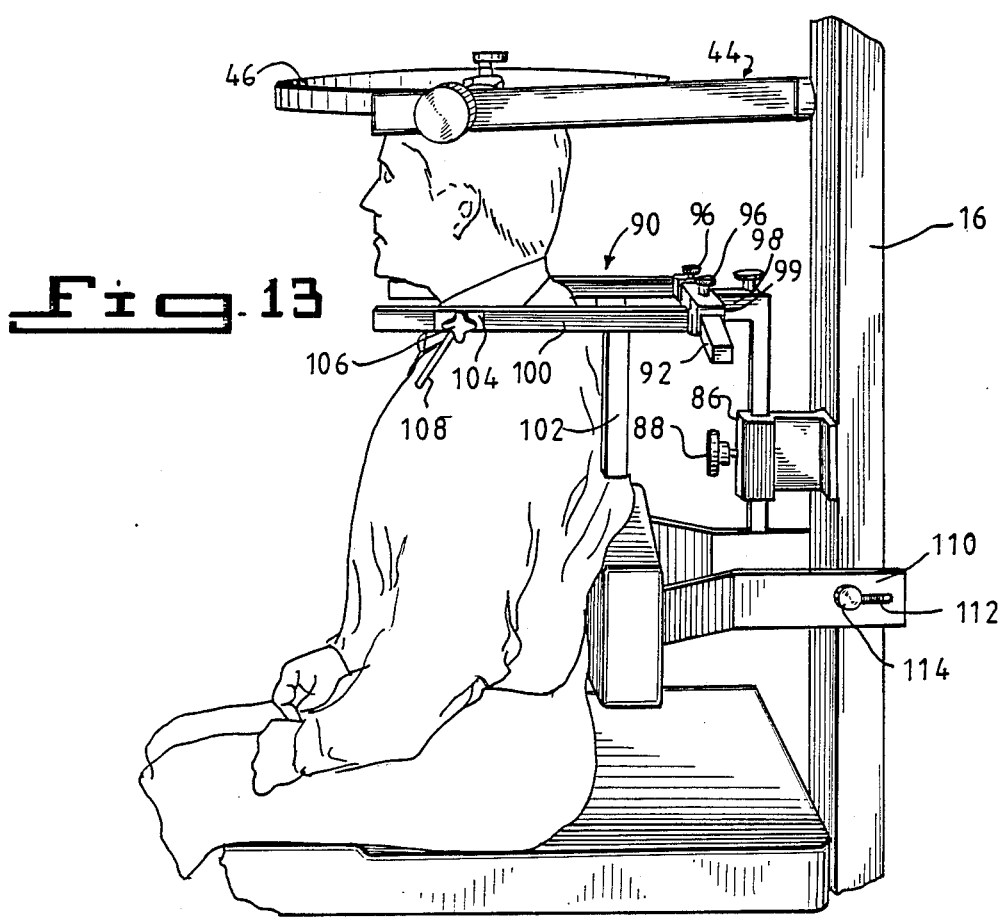
FIG. 13 is a side perspective view of an alternative embodiment of the invention.
Figure 14:
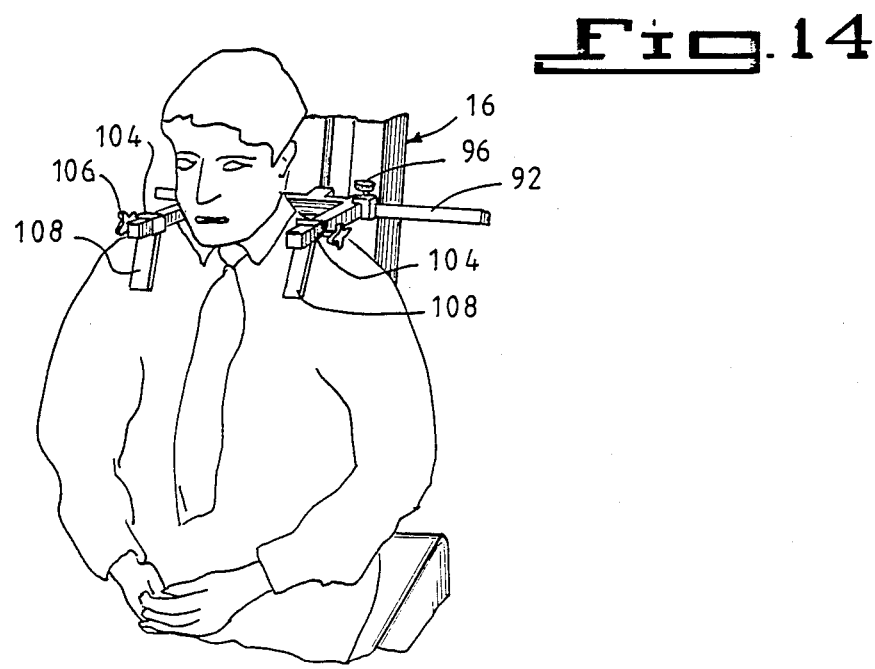
FIG. 14 is a front perspective view thereof.

The stabilizing assembly may alternatively be constructed from mechanical elements as shown in FIGS. 13-14. It may be mounted to the column by a vertically oriented rod which extends within a sleeve 86 secured to the column. A knob 88 is provided for moving a set screw within the sleeve 86, thereby maintaining the vertical position of the assembly. In accordance with this embodiment of the invention, the stabilizing assembly includes a shoulder stabilizer 90 including a horizontal cross piece 92 having a rectangular cross section. A pair of rectangular sleeves 94 are mounted near each end of the cross piece and locked in place by knob/screw assemblies 96. A rearwardly extending horizontal projection 98 from the center of the cross piece connects it to the vertically oriented rod within the column sleeve 86.

A pair of forwardly projecting, rectangular rods 100 extend, respectively, from the set of sleeves 94. Each rod includes a downwardly projecting rod 102 extending therefrom to which a cushion (not shown) may be mounted. A sleeve 104 is slidably mounted to each forwardly projecting rod 100. Each sleeve 104 is secured in position by a knob/screw assembly 106. A forwardly inclined chest restraining member 108 is secured to each sleeve 104. A restraining belt (not shown) extends about the seat back 18 and may be secured about the abdomen of a person seated upon the apparatus. A second belt (not shown) is secured beneath the seat and extends over the user's lap.

Figure 4:
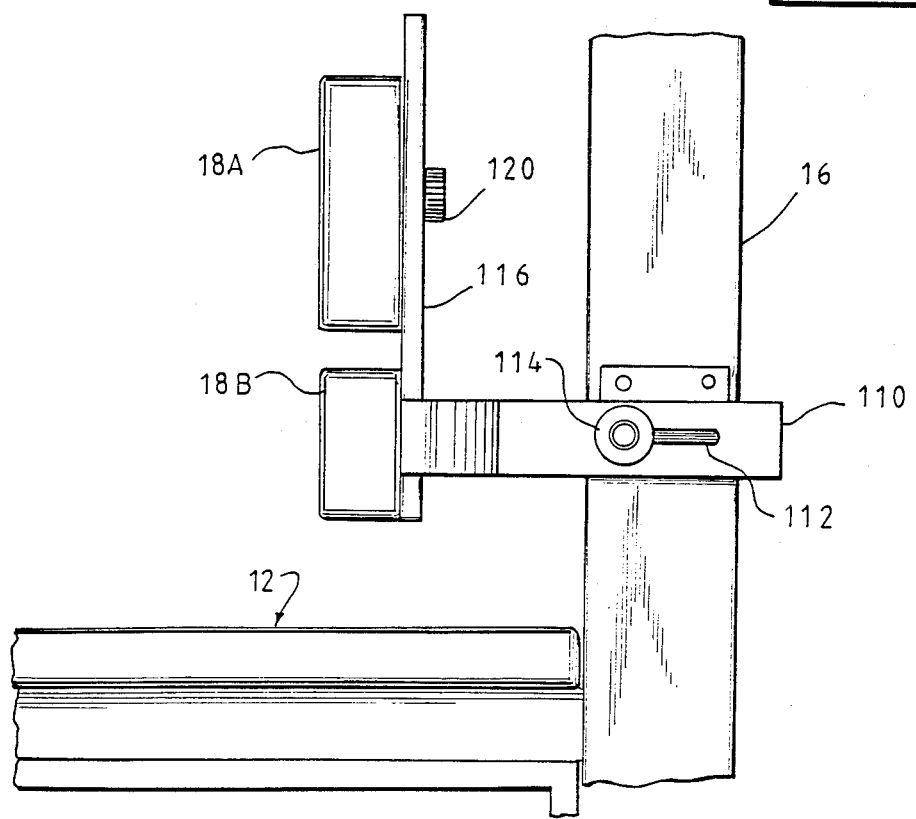
FIG. 4 is a side elevation view of the seat and back rest portions of the apparatus.
Figure 9:
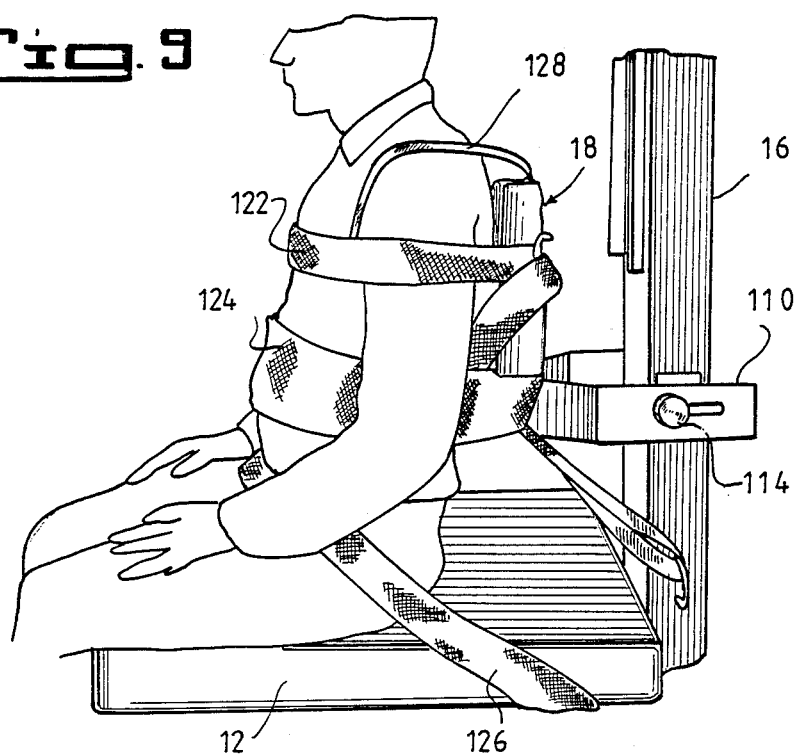
FIG. 9 is a side perspective view of a patient seated upon the apparatus.
Figure 10:
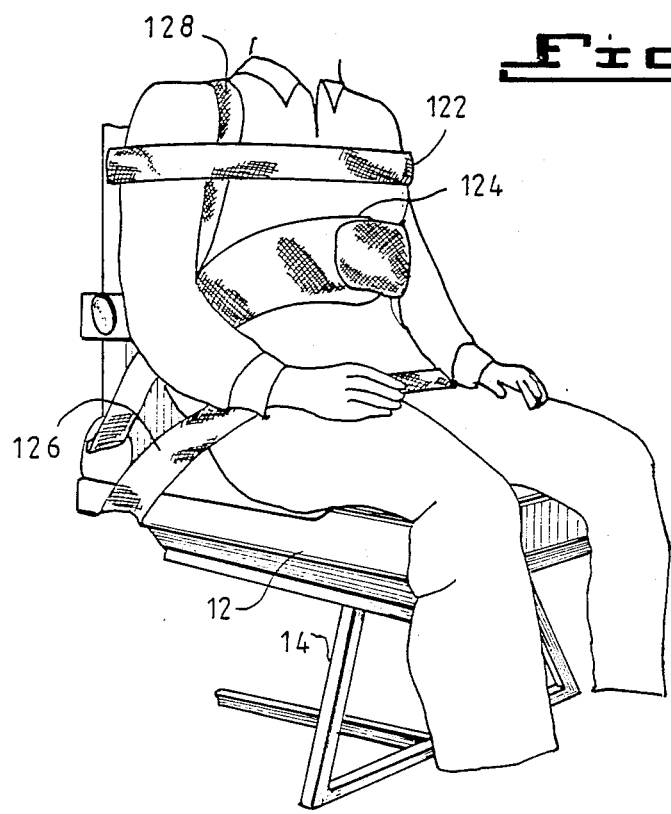
FIG. 10 is a front perspective view thereof.

Both sections of the seat back 18A, 18B shown in FIGS. 1 and 4, and the single seat back section shown in FIG. 13 are adjustable in position with respect to the column 16. A backrest support 110 is mounted to the column 16 and includes at least one horizontal slot 112 therein. A knob 114 having a threaded pin (not shown) extending therefrom is mounted to the column and is used for securing the backrest support 110 in the desired horizontal position. The support may include a vertically extending member 116 having one or more vertically oriented slots 118 therein for allowing the elevations of the backrest sections to be adjusted. Knobs 120 may be provided for securing the back supports in desired positions.

In operation, a person is seated upon the seat 12 of the apparatus while the pressure detection assembly and the stabilizing assembly are both in inactive positions where they do not interfere with the person. If the alternative stabilizing assembly is employed, the forwardly projecting rods 100 thereof are moved relatively far apart by positioning the sleeves 94 near the outer ends of the horizontal cross piece 92. The seat is relatively high, and includes an elevated front portion, so that the seated person's feet do not touch the floor. It is also relatively long to facilitate one's assuming the seated position.

The stabilizing assembly is moved into position adjacent to the patient's shoulders prior to tightening the first knob 88. Lateral adjustments are made by loosening knobs 96 and sliding sleeves 94 outwardly.

The chest restraining members 108 are then moved into position such that they are in contact with the patient's chest while the rods 100 contact the scapular area. Once all of the appropriate tightening knobs have been turned to secure the movable parts of the stabilizing assembly, the cervical muscles will be sufficiently isolated to allow them to be reliably tested.

If the preferred belted assembly is used for stabilizing the person, the belts 122, 124 and 126 are secured snugly about the upper chest, waist and pelvis. The shoulder belts 128 are tightened sufficiently to restrain the subject without exerting undue pressure upon the shoulders. The back is stabilized by the thoracic and lumbar supports 18A, 18B.

The support 44 for the testing assembly is lowered into position by loosening knob 40 and sliding the block assembly 30 downwardly along track 26. The knob 40 is tightened and the transducer positioning ring is moved to the desired angular position with respect to the horizontal plane. A first angular adjustment is made by loosening knob 52 to allow the pivot member 42 to rotate. The support, being secured to the pivot member, is moved to the desired angular position and fixed in place by turning the knob 52 in the appropriate direction.

The transducer positioning ring 46 is then rotated to a selected angular position with respect to the plane defined by the support. Knobs 62 are loosened to permit such rotation and thereafter tightened to maintain the ring in a fixed position. The arc of rotation of both the support 44 and ring 46 is preferably limited to about sixty degrees, which is sufficient for all exercise programs and testing to be done on the apparatus.

The transducer positioning member 48 is moved into the desired position on the ring 46 by loosening knob 70 and sliding it to one of the testing points indicated on the ring. The transducer 80 is then applied against the patient's head by sliding the plunger 72 with respect to the positioning member 48 and locking it at a desired point. If necessary, the height and angular orientation of the positioning member 48 are also adjusted by moving the adjustment rod 84 to the desired position prior to tightening the knob 84A.

Isometric therapy may be conducted by having the patient apply pressure against the transducer with his head for selected periods of time with a predetermined force. The patient may monitor the force himself by observing a visual display indicating the output of the pressure transducer.

The force applied during therapy is usually a selected fraction of the peak force of which the patient is capable. Since the shoulders and other parts of the body are well stabilized, the muscles which require exercise are isolated and can be exercised in a properly controlled program.

Testing of the cervical muscles can be accomplished in a similar manner. The tests are repeatable and accurate as recruitment of other muscle groups is substantially eliminated and the transducer can be located in the identical position for each test. The force generated by the patient, whether during an exercise program or testing, can be measured for each of the following neck movements: (1) anterior flex; (2) anterior oblique-right; (3) lateral-right; (4) rotation-right; (5) posterior oblique-right; (6) posterior-extended; (7) posterior oblique-left; (8) rotation-left, (9) lateral-left; (10) anterior oblique-left. The system can be adjusted to additional angles that may be desirable.

What is claimed is:

1. An apparatus for exercising or testing cervical muscles comprising:
    a transducer positioning member;
    a transducer positioning ring, said transducer positioning member being mounted to said transducer positioning ring;
    means for pivotably moving said transducer positioning ring about a first axis; and
    means for pivotably moving said transducer positioning ring about a second axis.

2. An apparatus as defined in claim 1 including means for adjusting the vertical position of said transducer positioning ring.

3. An apparatus as defined in claim 1 wherein said first axis is substantially perpendicular to said second axis.

4. An apparatus as defined in claim 1 including a pressure transducer mounted to said transducer positioning member.

5. An apparatus as defined in claim 4 including a plunger slidably mounted to said transducer positioning member and extending within said transducer positioning ring, said pressure transducer being secured to said plunger.

6. An apparatus as defined in claim 1 including a column, a support pivotably mounted to said column, said transducer positioning ring being pivotably mounted to said support.

7. An apparatus as defined in claim 6 including means for slidably mounting said support to said column.

8. An apparatus as defined in claim 7 wherein said support has a generally U-shaped configuration including a pair of opposing arms extending away from said column, said transducer positioning ring being positioned between said opposing arms and pivotably mounted thereto.

9. An apparatus as defined in claim 6 including a seat assembly mounted to said column.

10. An apparatus as defined in claim 6 including a shoulder stabilizing assembly mounted to said column beneath said support.

11. An apparatus as defined in claim 1 wherein said transducer positioning member is slidably mounted to said transducer positioning ring.

12. An apparatus for exercising or testing cervical muscles comprising:
    a seat;
    means for stabilizing the shoulders of a person seated upon said seat, said stabilizing means including first restricting means for preventing either shoulder from moving up or down and second restricting means for preventing either shoulder from moving forward or backward; and
    means for mounting a pressure sensing transducer adjacent to the head of a person seated upon said seat.

13. An apparatus as defined in claim 12 including a column, said seat, said stabilizing means and said mounting means being secured to said column.

14. An apparatus as defined in claim 13 wherein said stabilizing means includes a pair of rods extending forwardly with respect to said column.

15. An apparatus as defined in claim 14 including adjustment means for adjusting the vertical positions of said forwardly extending rods.

16. An apparatus as defined in claim 14 including a downwardly projecting rod extending from each of said forwardly extending rods and a chest restraining member extending downwardly from each of said forwardly extending rods.

17. An apparatus as defined in claim 16 including means for adjusting the distance between each of said respective downwardly projecting rods and said chest restraining members on each of said forwardly extending rods.

18. An apparatus as defined in claim 14 including means for adjusting the lateral distance between each of said forwardly extending rods.

19. An apparatus as defined in claims 12 wherein said mounting means includes a transducer positioning ring and a transducer positioning member mounted to said ring.

20. An apparatus as defined in claim 19 wherein said transducer positioning member is slidably mounted to said ring.

21. An apparatus as defined in claim 19 including means for pivotably moving said ring about a first axis and means for pivotably moving said ring about a second axis.

22. An apparatus as defined in claim 19 including a pressure transducer mounted to said transducer positioning member, and means for moving said pressure transducer radially with respect to said ring.

23. An apparatus as defined in claim 12 including a pressure transducer mounted to said mounting means.

24. An apparatus as defined in claim 23 wherein said mounting means includes a transducer positioning ring, said pressure transducer being slidably mounted to said ring, and means for pivotably moving said transducer positioning ring about a first axis.

25. An apparatus as defined in claim 24 including means for pivotably moving said transducer positioning ring about a second axis.

26. A method of determining the force exerted by a cervical muscle group comprising the steps of:
 seating a person;
 restricting the person's shoulders from moving up, down, forwardly or rearwardly; and
 positioning a pressure transducer adjacent the person's head, whereby the person's cervical muscles are substantially isolated from the other muscles of the person such that pressure exerted by the person against the pressure transducer is substantially entirely due to the contraction of a cervical muscle group.

27. A method as defined in claim 26 wherein said person is seated such that his feet are suspended.

* * * * *